(12) United States Patent
Liang et al.

(10) Patent No.: US 7,871,568 B2
(45) Date of Patent: Jan. 18, 2011

(54) RAPID TEST APPARATUS

(75) Inventors: Greg Liang, Rancho Cucamonga, CA (US); Yahong Liang, Rancho Cucamonga, CA (US)

(73) Assignee: Quidel Corporation, San Diego, CA (US)

( * ) Notice: Subject to any disclaimer, the term of this patent is extended or adjusted under 35 U.S.C. 154(b) by 636 days.

(21) Appl. No.: 11/625,813

(22) Filed: Jan. 22, 2007

(65) Prior Publication Data
US 2007/0275475 A1 Nov. 29, 2007

Related U.S. Application Data

(60) Provisional application No. 60/761,580, filed on Jan. 23, 2006.

(51) Int. Cl.
G01N 21/00 (2006.01)
G01N 31/22 (2006.01)
G01N 15/06 (2006.01)
G01N 33/00 (2006.01)
G01N 33/48 (2006.01)
G01N 1/10 (2006.01)
B01L 3/00 (2006.01)

(52) U.S. Cl. ............... 422/58; 422/55; 422/61; 422/68.1; 422/102; 436/180

(58) Field of Classification Search ............... 422/58
See application file for complete search history.

(56) References Cited

U.S. PATENT DOCUMENTS

| | | | |
|---|---|---|---|
| 3,660,033 A | * | 5/1972 | Schwartz ............... 436/174 |
| 3,992,158 A | | 11/1976 | Przybylowicz et al. |
| 4,275,149 A | | 6/1981 | Litman et al. |
| 4,299,916 A | | 11/1981 | Litman et al. |
| 4,353,868 A | * | 10/1982 | Joslin et al. ............... 422/101 |
| 4,366,241 A | | 12/1982 | Tom et al. |
| 4,373,932 A | | 2/1983 | Gribnau et al. |
| 4,426,451 A | | 1/1984 | Columbus |
| 4,587,099 A | | 5/1986 | Rothe et al. |
| 4,632,901 A | | 12/1986 | Valkirs et al. |
| 4,643,560 A | | 2/1987 | Morse |
| 4,695,554 A | | 9/1987 | O'Connell et al. |

(Continued)

FOREIGN PATENT DOCUMENTS

EP  0 249 418 A2  12/1987

(Continued)

OTHER PUBLICATIONS

The International Search report and Written Opinion for PCT Application PCT/US2007/001678, 8 pages, Search Report dated Sep. 26, 2007 (2007).

(Continued)

*Primary Examiner*—Jill Warden
*Assistant Examiner*—Charles Hammond
(74) *Attorney, Agent, or Firm*—Judy M. Mohr; LeeAnn Gorthey; King & Spalding LLP

(57) ABSTRACT

Provided herein are methods and devices for rapid testing of solid, semi-solid, or liquid specimens, such as stool, blood, urine, saliva, or swab specimens of the cervix, urethra, nostril, and throat, and for environmental testing.

12 Claims, 3 Drawing Sheets

U.S. PATENT DOCUMENTS

Figure 8:
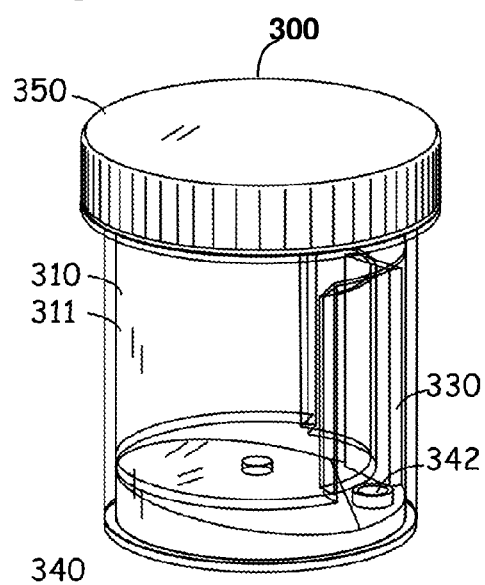

| | | | |
|---|---|---|---|
| 4,702,017 A | 10/1987 | Leinhardt | |
| 4,703,017 A | 10/1987 | Campbell et al. | |
| 4,806,311 A | 2/1989 | Greenquist | |
| 4,824,640 A | 4/1989 | Hildebrand et al. | |
| 4,863,875 A | 9/1989 | Bailey et al. | |
| 4,916,056 A | 4/1990 | Brown, III et al. | |
| 4,943,522 A | 7/1990 | Eisinger et al. | |
| 4,945,205 A | 7/1990 | Litman et al. | |
| 4,999,285 A | 3/1991 | Stiso | |
| 5,008,080 A | 4/1991 | Brown, III et al. | |
| 5,075,078 A | 12/1991 | Osikowicz et al. | |
| 5,096,837 A | 3/1992 | Fan et al. | |
| 5,110,550 A | 5/1992 | Schtipfenbacher et al. | |
| 5,120,643 A | 6/1992 | Ching et al. | |
| 5,145,789 A | 9/1992 | Corti et al. | |
| 5,149,622 A | 9/1992 | Brown et al. | |
| 5,160,021 A | 11/1992 | Sibley et al. | |
| 5,160,701 A | 11/1992 | Brown, III et al. | |
| 5,208,166 A | 5/1993 | Saunders et al. | |
| 5,223,220 A | 6/1993 | Fan et al. | |
| 5,266,497 A | 11/1993 | Imai et al. | |
| 5,268,148 A * | 12/1993 | Seymour | 422/101 |
| 5,275,785 A | 1/1994 | May et al. | |
| 5,283,038 A * | 2/1994 | Seymour | 422/101 |
| 5,338,513 A | 8/1994 | Schtipfenbacher et al. | |
| 5,356,782 A | 10/1994 | Moorman et al. | |
| 5,401,667 A | 3/1995 | Koike | |
| 5,415,994 A | 5/1995 | Imrich et al. | |
| 5,458,852 A | 10/1995 | Buechler | |
| 5,468,647 A | 11/1995 | Skold et al. | |
| 5,504,013 A | 4/1996 | Senior | |
| 5,516,644 A | 5/1996 | Yamauchi et al. | |
| 5,521,102 A | 5/1996 | Boehringer et al. | |
| 5,571,726 A | 11/1996 | Brooks, Jr. et al. | |
| 5,591,645 A | 1/1997 | Rosenstein | |
| 5,602,040 A | 2/1997 | May et al. | |
| 5,622,871 A | 4/1997 | May et al. | |
| 5,624,809 A | 4/1997 | Skold et al. | |
| 5,656,503 A | 8/1997 | May et al. | |
| 5,712,170 A | 1/1998 | Kouvonen et al. | |
| 5,712,172 A | 1/1998 | Huang et al. | |
| 5,714,389 A | 2/1998 | Charlton et al. | |
| 5,714,728 A | 2/1998 | Brooks, Jr. et al. | |
| 5,726,010 A | 3/1998 | Clark | |
| 5,763,262 A | 6/1998 | Wong et al. | |
| 5,766,961 A | 6/1998 | Pawlak et al. | |
| 5,770,460 A | 6/1998 | Pawlak et al. | |
| 5,773,234 A | 6/1998 | Pronovost et al. | |
| 5,786,220 A | 7/1998 | Pronovost et al. | |
| 5,800,779 A | 9/1998 | Johnson | |
| 5,804,452 A | 9/1998 | Pronovost et al. | |
| 5,827,675 A * | 10/1998 | Skiffington et al. | 435/8 |
| 5,877,028 A | 3/1999 | Chandler et al. | |
| 5,885,527 A | 3/1999 | Buechler | |
| 5,895,765 A | 4/1999 | Rheinheimer et al. | |
| 5,962,333 A | 10/1999 | Incorvia et al. | |
| 5,965,458 A | 10/1999 | Kouvonen et al. | |
| 5,989,921 A | 11/1999 | Charlton et al. | |
| 5,998,156 A | 12/1999 | Sugiyama | |
| 6,019,944 A | 2/2000 | Buechler | |
| 6,057,166 A | 5/2000 | Childs et al. | |
| 6,087,184 A | 7/2000 | Magginetti et al. | |
| 6,113,855 A | 9/2000 | Buechler | |
| 6,120,733 A * | 9/2000 | Goodman et al. | 422/61 |
| 6,143,576 A | 11/2000 | Buechler | |
| 6,156,270 A | 12/2000 | Buechler | |
| 6,165,798 A | 12/2000 | Brooks | |
| 6,180,417 B1 | 1/2001 | Hajizadeh et al. | |
| 6,187,268 B1 | 2/2001 | Albarella et al. | |
| 6,187,369 B1 | 2/2001 | Beavers | |
| 6,194,221 B1 | 2/2001 | Rehg et al. | |
| 6,194,222 B1 | 2/2001 | Buechler et al. | |
| 6,207,113 B1 * | 3/2001 | Kagaya | 422/102 |
| 6,210,898 B1 | 4/2001 | Bouma et al. | |
| 6,228,658 B1 | 5/2001 | Fornica et al. | |
| 6,228,660 B1 | 5/2001 | May et al. | |
| 6,248,294 B1 * | 6/2001 | Nason | 422/58 |
| 6,271,040 B1 | 8/2001 | Buechler | |
| 6,284,198 B1 | 9/2001 | Kirollos et al. | |
| 6,297,060 B1 | 10/2001 | Nowakowski et al. | |
| 6,316,205 B1 | 11/2001 | Guan et al. | |
| 6,352,862 B1 | 3/2002 | Davis et al. | |
| 6,391,265 B1 | 5/2002 | Buechler et al. | |
| 6,399,398 B1 | 6/2002 | Cunningham et al. | |
| 6,406,920 B1 | 6/2002 | Davis et al. | |
| 6,410,341 B1 | 6/2002 | Freitag et al. | |
| 6,436,722 B1 | 8/2002 | Clark et al. | |
| 6,485,982 B1 | 11/2002 | Charlton | |
| 6,534,320 B2 | 3/2003 | Ching et al. | |
| 6,537,505 B1 | 3/2003 | LaBudde et al. | |
| 6,548,019 B1 * | 4/2003 | Lee et al. | 422/58 |
| 6,605,476 B2 | 8/2003 | Kobayashi | |
| 6,613,405 B1 | 9/2003 | Hekal | |
| 6,656,744 B2 | 12/2003 | Pronovost et al. | |
| 6,656,745 B1 | 12/2003 | Cole | |
| 6,663,833 B1 | 12/2003 | Stave et al. | |
| 6,669,907 B1 | 12/2003 | Buechler | |
| 6,673,628 B2 | 1/2004 | Freitag et al. | |
| RE38,430 E | 2/2004 | Rosenstein | |
| 6,686,170 B1 | 2/2004 | Flanders et al. | |
| 6,689,317 B1 | 2/2004 | Rees | |
| 6,699,722 B2 | 3/2004 | Bauer et al. | |
| 6,726,879 B2 * | 4/2004 | Ng et al. | 422/58 |
| 6,730,494 B1 | 5/2004 | Toranto et al. | |
| 6,737,278 B1 | 5/2004 | Carlsson et al. | |
| 6,780,160 B2 | 8/2004 | Zhou et al. | |
| 6,805,837 B2 * | 10/2004 | Tydings | 422/58 |
| 6,855,561 B2 | 2/2005 | Jerome et al. | |
| 6,921,370 B2 | 7/2005 | Zhou et al. | |
| 6,924,153 B1 | 8/2005 | Boehringer et al. | |
| 7,005,459 B2 | 2/2006 | Hekal | |
| 7,163,514 B2 | 1/2007 | Zhou et al. | |
| 7,485,262 B2 * | 2/2009 | DiCesare et al. | 422/61 |
| 7,550,112 B2 * | 6/2009 | Gou et al. | 422/58 |
| 2002/0086436 A1 | 7/2002 | Buechler | |
| 2002/0098532 A1 | 7/2002 | Yee | |
| 2003/0035758 A1 | 2/2003 | Buechler et al. | |
| 2003/0157699 A1 | 8/2003 | Jerome et al. | |
| 2003/0161762 A1 | 8/2003 | Caron et al. | |
| 2003/0211634 A1 | 11/2003 | Jerome et al. | |
| 2004/0002165 A1 | 1/2004 | Buchanan et al. | |
| 2004/0059256 A1 | 3/2004 | Perez | |
| 2004/0060374 A1 * | 4/2004 | Goodin | 73/864.51 |
| 2004/0077103 A1 | 4/2004 | Buechler | |
| 2004/0152207 A1 | 8/2004 | Nelson et al. | |
| 2005/0048670 A1 * | 3/2005 | Wu et al. | 436/180 |
| 2005/0119589 A1 * | 6/2005 | Tung et al. | 600/584 |
| 2005/0163660 A1 | 7/2005 | Wang | |
| 2005/0181518 A1 | 8/2005 | Chandler | |
| 2005/0227371 A1 | 10/2005 | Gokhan | |
| 2006/0029517 A1 * | 2/2006 | Hartselle | 422/61 |
| 2006/0062690 A1 | 3/2006 | Lawrence | |
| 2006/0078986 A1 | 4/2006 | Ly et al. | |
| 2006/0210448 A1 * | 9/2006 | Wang et al. | 422/102 |
| 2007/0065339 A1 * | 3/2007 | Huff | 422/58 |
| 2007/0092402 A1 * | 4/2007 | Wu et al. | 422/58 |
| 2008/0019867 A1 | 1/2008 | Johnson et al. | |
| 2008/0272283 A1 | 11/2008 | Feldsine et al. | |
| 2009/0004058 A1 | 1/2009 | Liang et al. | |

FOREIGN PATENT DOCUMENTS

| | | |
|---|---|---|
| EP | 0 258 963 A2 | 3/1988 |
| EP | 0 260 965 A2 | 3/1988 |

| | | |
|---|---|---|
| EP | 0 353 500 A2 | 2/1990 |
| EP | 0 383 819 B1 | 4/1997 |
| EP | 0 903 584 A1 | 3/1999 |
| EP | 1 046 913 A2 | 10/2000 |
| EP | 1 046 913 A3 | 10/2000 |
| EP | 1 174 716 A2 | 1/2002 |
| EP | 1 174 716 A3 | 1/2002 |
| EP | 1 248 112 A2 | 10/2002 |
| EP | 0 833 157 A1 | 11/2002 |
| EP | 0 291 194 B2 | 7/2003 |
| EP | 1 327 884 A1 | 7/2003 |
| EP | 0 901 630 B1 | 8/2003 |
| EP | 1 376 131 A1 | 1/2004 |
| EP | 1 754 971 A1 | 2/2007 |
| GB | 2404735 A * | 2/2005 |
| WO | WO88/08534 A1 | 11/1988 |
| WO | WO89/04156 A1 | 5/1989 |
| WO | WO92/21977 A1 | 12/1992 |
| WO | WO95/13542 A1 | 5/1995 |
| WO | WO97/06437 A1 | 2/1997 |
| WO | WO97/26083 A1 | 7/1997 |
| WO | WO97/44664 A1 | 11/1997 |
| WO | WO99/47930 A1 | 9/1999 |
| WO | WO00/63697 A1 | 10/2000 |
| WO | WO01/57522 A2 | 8/2001 |
| WO | WO02/50609 A2 | 6/2002 |
| WO | WO02/50609 A3 | 6/2002 |
| WO | WO2004/011942 A1 | 2/2004 |
| WO | WO2005/095967 A1 | 10/2005 |
| WO | WO2006/005483 A1 | 1/2006 |
| WO | WO2007/087261 A2 | 8/2007 |
| WO | WO2007/098184 A2 | 8/2007 |
| WO | WO2007/105680 A1 | 9/2007 |
| WO | WO 2009/011869 A1 | 1/2009 |

OTHER PUBLICATIONS

The International Search report and Written Opinion for PCT Application PCT/US2009/002542, Search Report dated Jul. 24, 2009, 15 pages (2009).

U.S. Appl. No. 12/390,303, Kirby, Kevin, Not published.

Lindberg, Roy A., "Plastic-Molding Processes", Chapter 10 in *Processes and Materials of Manufacture* 3$^{rd}$ ed., Allyn an d Bacon, Boston pp. 393-432 (1983).

Odexxo Company, Product Description from Odexxo Company Website "All-in-One Fecal Sample Collecting Device", 3 pages, http://www.odexxo.com (2008).

* cited by examiner

Fig. 1
Fig. 2
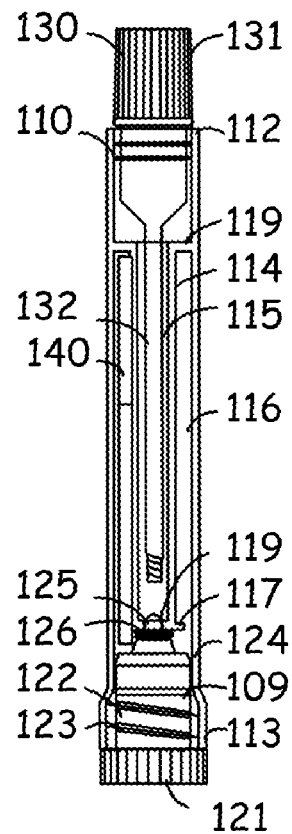
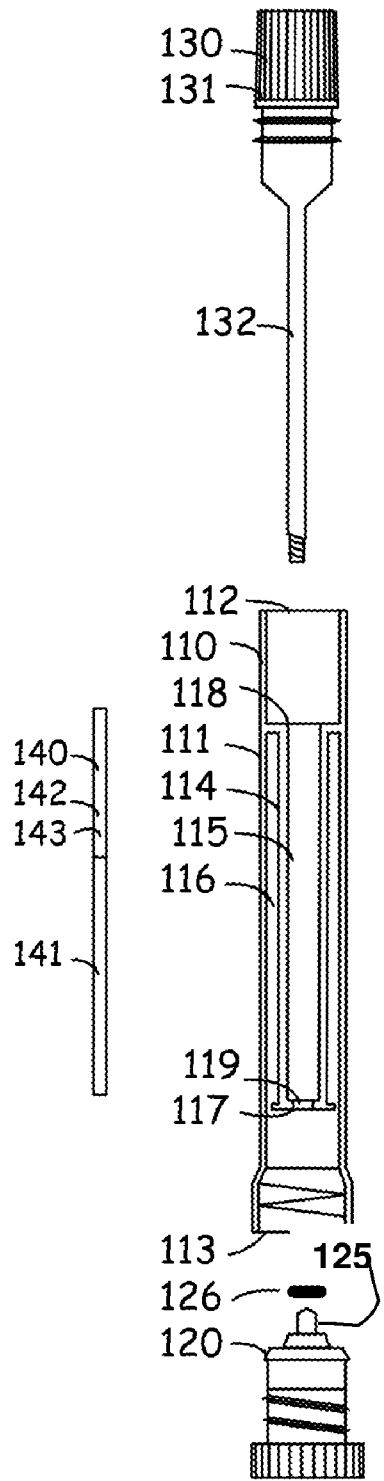

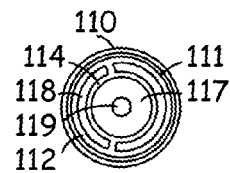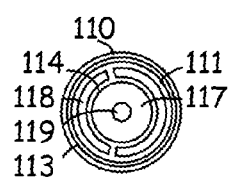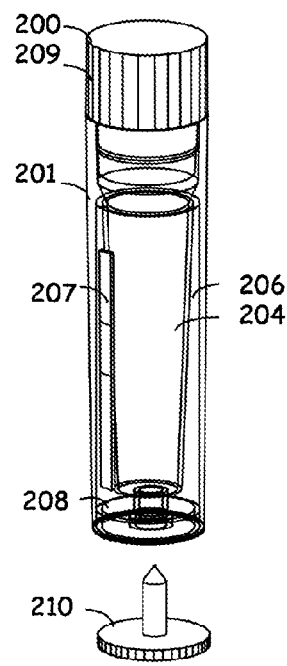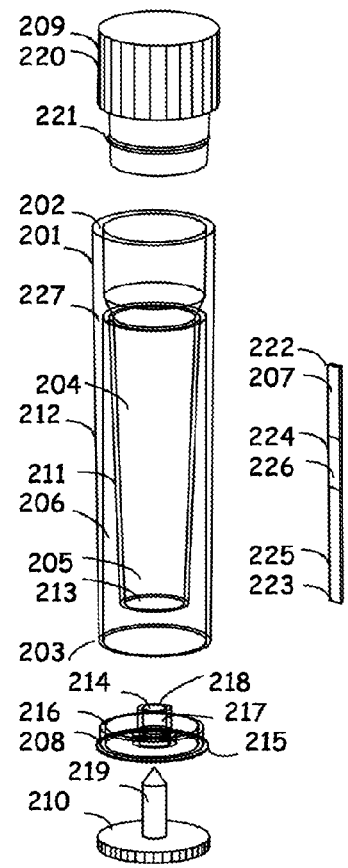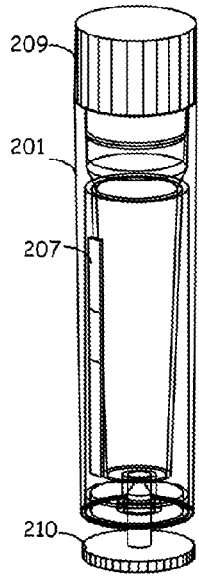

RAPID TEST APPARATUS

PRIORITY

Priority is claimed to U.S. Provisional Application No. 60/761,580, by Greg Liang and Yahong Liang, filed Jan. 23, 2006, entitled Rapid Test Apparatus, which is referred to and is hereby incorporated by reference herein in its entirety.

FIELD OF THE INVENTION

The invention is in general directed to methods and devices for rapid testing of solid, semi-solid, or liquid specimens, such as stool, blood, urine, saliva, or swab specimens of the cervix, urethra, nostril, and throat, and for rapid testing of environmental samples.

BACKGROUND

The testing of solid, semi-solid, or liquid specimens such as stool, blood, urine, saliva, or swab specimens of the cervix, urethra, nostril, or throat, as well as environmental specimens, such as food products, soil and dust, often requires pre-treating the specimens with a test buffer. Pre-treating the specimens helps to dilute the specimen, extract substances to be detected from the specimen, or alter the specimen or substances. This pre-treatment results in a new sample solution that is more suitable for the test substance to be detected. Typically, the collected specimen is pre-mixed with the test buffer in a container separate from the test device used to detect the presence of a particular test substance. In most testing protocols, a portion of the resulting sample solution is transferred to a second test location for reacting with a reagent to obtain a test result that indicates the presence or quantity of the test substance in the specimen. For example, in a fecal occult blood test, a plastic tube is used to suspend the fecal specimen in a test buffer, which dissolves the blood components of the specimen. A breakable part of the plastic tube is then severed and a portion of the sample solution is released from the tube to a second device, which is used to conduct an immunological hemoglobin test. The test result is read at a test area of the test device.

The procedures for severing the specimen treatment tube and transferring the sample solution from the specimen treatment tube to the test device complicates the test methods by requiring multiple steps. By requiring that the sample be transferred, the work area may be contaminated due to sample leakage. Also, transferring the sample solution may lead to inaccurate results because of the possible transfer of inaccurate test volumes. These methods are not convenient for onsite testing by non-laboratory trained users. What is needed is a more simple, safe, and accurate method of testing of solid, semi-solid, or liquid specimens.

SUMMARY

The present invention provides devices and methods for treating and testing specimens that are simpler, safer to use, and more accurate. In certain embodiments of the present invention are provided test assemblies that may be used for rapid testing of solid, semi-solid, or liquid specimens. In one non-limiting embodiment is provided a rapid test device for testing the presence of fecal occult blood. In this embodiment of the invention, feces sample collection, treatment, and testing are performed all in one device. For example, a test buffer is pre-stored in the device in a sample receiving chamber, and at least one rapid lateral flow test strip for detecting hemoglobin is stored in a separate test chamber, the test chamber. A sampling stick is attached to the upper cap of the device for stool sample collection, and the feces specimen is transferred to the test buffer chamber using the sampling stick. The device is then shaken to distribute the feces sample into the buffer, and the test is initiated by twisting a cap at the bottom of the device, allowing the sample solution to contact a lateral flow test strip. The visual test result may then be read from the lateral flow test strip within about 5 minutes.

In one embodiment is provided a test device comprising a test assembly, wherein the test assembly may be, for example, longitudinal, having an upper end, a lower end, a sample receiving chamber that has an opening at the upper end of the test assembly, a test chamber having an opening at the lower end of the test assembly and capable of receiving a reagent member from the opening, a base capable of being coupled to the opening of the test chamber and sealing the lower end of the test assembly with the reagent member inside the test chamber, and a means for liquid communication from the sample receiving chamber to the test chamber that exists when the base is attached to the test assembly containing the reagent member inside the test chamber. The test assembly may be any form having various appropriate dimensions for specimen collection and testing, and may, for example, be in the form of a cup, or, for example, a tube. The testing devices of the present invention, for example, the test assembly, may be of any suitable material, including, for example, plastic, such as, for example, a plastic selected from the group consisting of polyethylene, polypropylene, polystyrene, polyvinyl, and acrylonitrile butadiene styrene.

Also disclosed is a diagnostic testing device comprising a longitudinal test assembly having an upper end, a lower end, a sample receiving chamber that has an opening at the upper end of the test assembly, a test chamber having an opening at the lower end of the test assembly and capable of receiving a reagent member from the opening, a reagent member inside the test chamber, a base coupled to the opening of the test chamber, wherein the base seals the lower end of the test assembly with the reagent member inside the test chamber, and a means for liquid communication from the sample receiving chamber to the test chamber.

The method for using the test assembly to make a diagnostic testing device comprises introducing a reagent member capable of reacting with an assay sample and producing a signal indicating the presence or quantity of an analyte of the assay sample into the test chamber from the lower end of the test assembly and attaching the base to the lower end of the test chamber.

The method for using a testing device of the invention comprises introducing a sample solution into the sample receiving chamber, activating the sample communication means from the sample receiving chamber to the test chamber and reading the test result of the reagent member.

The test device of the invention may be used, for example, for testing analytes selected from a group of analytes consisting of but not limited to drugs of abuse, hormones, tumor markers, cardiac markers, infectious pathogens, and environmental pollutants. The test sample solution is a solution, which is suspected of containing certain levels of the analyte. Such sample solution is selected from a group of solutions including body fluids including urine, saliva, plasma or serum, blood, and spinal fluid. The sample solution may also contain a treatment solution, such as water, pH or protein buffer. For example, dust or powders suspected of containing drugs, explosives, or infectious substances may be dissolved in water or a pH buffer solution for testing, using a device of the invention.

DETAILED DESCRIPTION OF THE DRAWINGS

Figure 9:
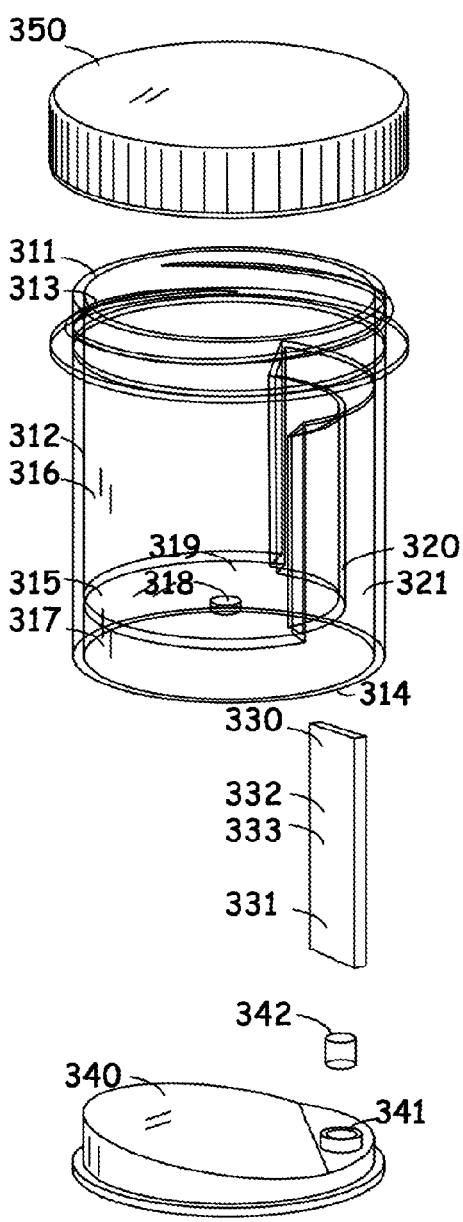

FIG. 1 is a side view of a device of the invention.
FIG. 2 is an exploded view of the same device of FIG. 1.
FIG. 3 is a top view of a test assembly of the invention.
FIG. 4 is a bottom view of the same part of FIG. 3.
FIG. 5 is an elevated perspective view of another device of the invention.
FIG. 6 is an exploded view of the same device of FIG. 5.
FIG. 7 is an elevated perspective view of the sample device of FIG. 5 in a test position.
FIG. 8 is a perspective view of a device of the invention.
FIG. 9 is an exploded view of the same device of FIG. 8.

DESCRIPTION

FIG. 1, in conjunction with FIG. 2 through FIG. 4, depicts a device of the invention. The sample collection and testing device comprises a testing assembly 110 and a base 120.

The test assembly 110 is longitudinal having wall 111, upper end 112, lower end 113, and septum wall 114 separating the interior of the test assembly into two chambers, a sample receiving chamber 115, and test chamber 116. The septum wall has a bottom section 117 that bends away from the exterior wall 111 and a top section 118 that connects to the exterior wall 111. The bottom section 117 of the septum wall comprises a hole 119, a bottom opening of the sample receiving chamber. The exterior wall has thread 109 on the interior side at the bottom end.

The base 120 comprises a handle section 121, insert section 122 having thread 123 and plug 125 for sealing off the bottom opening of the sample receiving chamber. Rubber o-ring 124 around the insert section 122 serves as a sealant.

In this embodiment, The reagent member 140 comprises a wick section 141 and a test area 142 comprising an assay reagent 143. When a sample solution contacts the wick section of the reagent member, the sample solution wicks up the wick section to the test area and reacts with the reagent. As a result, the presence or quantity of the test substance in the sample solution is detected.

A rubber o-ring 126 is provided as a sealant that closes the hole 119.

Optional cap 130 comprises handle 131, and sampler pin 132.

With an assay reagent member 140 inserted in the test chamber 116, the base is capable of tightly fitting to the bottom end of the test assembly, sealing off the bottom end of the test assembly, with the plug 125 and the o-ring 16 capable of sealing off the bottom opening of the sample receiving chamber.

When a sample solution is introduced into the sample receiving chamber, loosening the base 120 opens up the plug 125 and the o-ring 126 from the hole 119 and allows the sample solution to flow through the hole 119 and contact the reagent member 140 of the test chamber 116. The assay result of the sample solution, on the assay reagent member 140, can be read through the wall 111 at the test chamber section.

There are several options for this device to adapt to specific needs. First, with the reagent member inserted inside the test chamber, the base fitting into the bottom end of the test assembly with the plug 125 sealing off the bottom opening of the sample receiving chamber, a sample solution can be kept inside, or stored, inside the sample receiving chamber for future testing. Thus, a sample solution may be prepared, and the test conducted at a later time. For example, a patient may obtain a sample and the device may then be given to a laboratory technician, or other trained personnel for conducting the test and interpreting the results. Alternatively, a buffer solution for treating or diluting a test sample can be kept inside the sample receiving chamber before the sample is introduced into the sample receiving chamber. Secondly, the plug 125 or o-ring of the base 120 can be omitted from the device or the base be kept loose so that the passage between the sample receiving chamber and the test chamber is kept open. When a sample solution is introduced into the sample receiving chamber, a volume of the sample solution automatically flows from the sample receiving chamber into the test chamber through the sample passage or hole at the bottom section of the test assembly.

The optional cap 130 seals off the top opening of the sample receiving chamber. Its optional sampler pin is capable of collecting liquid or non-liquid samples and introducing the sample into the sample receiving chamber. Liquid samples include, for example, but are not limited to, blood, urine, saliva, water, mucus, or other fluid samples. Non-liquid samples include, for example, powder, stool, dirt, dust, and other dry or semi-dry samples.

Other means for permitting liquid communication from the sample-receiving chamber to the test chamber may be employed in the device. For example, simple modification to the device of FIG. 1 is, in one embodiment, a test assembly of the invention wherein the hole 119 is sealed or plugged, comprising a pin or other sharp edge or protrusion connected to the top surface of the base that is capable of breaking the seal or removing the plug when the base is turned or pushed against the test assembly. In this embodiment, the sample solution flows through the hole once the seal is broken or plug is removed, or, in another embodiment, the solution flows through the hole after the seal is broken of plug removed. In this embodiment, in one example, the hole is sealed when the cap is loosely fitted, and is unsealed when the cap is tightened, breaking the seal with the pin.

FIG. 5, in conjunction with FIG. 6 and FIG. 7, depicts another embodiment of the present invention. Device 200 comprises a test assembly 201 comprising an upper end 202 and a lower end 203, a sample receiving chamber 204 comprising a test buffer 205 and a test chamber 206 comprising a reagent member 207. A bottom part 208 closes the lower end of the test assembly 201, a cap 209 closes the upper end of the test assembly, and a means, such as a pincap 210 is provided for enabling liquid flow from the sample receiving chamber 204 to the test chamber 206. The test assembly 201 comprises a plastic tube structure comprising a tubular interior wall 211 and exterior wall 212 that join together at the neck area 227. The double layer sidewall forms an interior sample receiving chamber 204 and a test chamber 206. A breakable seal 213 seals off the lower end opening of the interior wall 211. The bottom part 208 sized to fit the lower end of the test assembly seals off the test assembly 206 from the lower end. The bottom part 208 comprises an upper end 214 and lower end 215, a sidewall 216 for fitting to the interior of the lower end of the test assembly, and a through hole 217 sealed off by a breakable seal 218 at the upper end 214. The pincap 210 comprises a rod 219 sized to fit into the through hole 217 of the bottom part and capable of breaking the breakable seals 218 and 213 when forced into the through hole from the lower end of the through hole. The cap 209 comprises a handle section 220 and an insert section 221 sized to fit to the upper opening 202 of the test assembly and closes the upper end of the assembly.

The reagent member 207 comprises an upper end 222 and lower end 223, a test area 224 proximal to the upper end 222 and a wick section 225 proximal to the lower end 223. The test area comprises at least one reagent 226. A liquid in contact with the wick section 225 is capable of wicking through the wick section to the test area 224 and contacting the reagent 226. The reagent member is disposed inside the test chamber with the upper end oriented towards the upper end of the test assembly and with the lower end of the reagent member oriented to the lower end of the test assembly.

The breakable seals of the test assembly are a hydrophobic barrier selected from a group consisting of plastic, rubber, and foil, attached to the sidewall of the sample receiving chamber. The seal breaking means for breaking the breakable seal includes any means capable of penetrating, tearing, or removing a portion of the breakable seal when the device is in a test position. In an embodiment of the invention, the seal breaking means is a stick inserted from the upper end of the sample receiving chamber capable of breaking the seal. The stick, in exemplary embodiments, is designed to be sanitary, that is, to not contaminate the specimen or sample solution. In another embodiment of the invention, the seal breaking means is a structure attached to the test module container capable of breaking the seal from the lower end of the sample receiving chamber.

FIG. 8, in conjunction with FIG. 9, depicts a device of another embodiment of the invention. The device 300 comprises an assembly 310 comprising a cup shaped transparent part 311 having an exterior wall or side wall 312, upper opening 313, lower opening 314, and a septum 315. The septum 315 is connected to the side wall 312 and separates the cup interior into an upper section 316 and a lower section 317 connected through a through-hole 318. A septum comprises a section 319 that is at an angle with the side wall and another section 320 that bends upward to form a pocket 321, a reagent member receptacle, with the side wall. The reagent member receptacle 321 contains a reagent member, an absorbent test strip comprising a wick section 331, a test area 332 comprising a reagent 333. A bottom part 340 is sized to fit to the lower opening of the cup part with the reagent member inside the reagent member receptacle. A vent hole 341 is a through hole of the bottom part 340. A porous plug 342 that is air permeable and sample solution impermeable fills in the through hole 341. An optional cap 350 is sized properly to fit to the upper opening 313.

The porous plug comprises a porous material of the desired property—air permeable and sample solution impermeable. Those of ordinary skill in the art are familiar with materials that may be used to form the porous plastic plug, such as, for example, but not limited to, polyethylene and polytetrafluoroethylene. The median pore size in the porous plastic plug may range from 3 microns to an upper limit which is dependent on the hydrophobicity of the plug material. Air and liquid permeability of porous plugs is related to the pore size and the surface property of the porous material. To achieve the desired property, the pore size of the plug is generally smaller than 30 microns, for example, 10-20 microns. Coating the surface of the porous material with a layer that will melt and forms a gel upon contact with the sample solution is another way to achieve the desired property. Such gel forming material can be selected from a group consisting gum, gelatin, long change polysaccharides, and proteins.

The reagent member may comprise more than one test reagent for detecting more than one test substance in the sample solution. For example, the device 300 may contain more than one absorbent test strip each for detecting a different test substance, such as a drug of abuse. When a sample solution, such as a urine specimen, is introduced into the device from the upper opening, the samples flows to the lower section of the device and reacts with the reagents. Therefore, multiple test substances, such as drugs of abuse, can be detected simultaneously. When the liquid level in the lower section of the device reaches the porous plug, the air vent through the plug closes. Additional liquid flow from the upper section to the lower section stops. Such a mechanism forms an automatic control of the volume of liquid flows into the test chamber.

The devices of the invention can be used, for example, for testing body fluid samples, environmental samples, stool, and other samples. Substances can be tested using the devices of the invention include drugs of abuse, therapeutic drugs, infectious pathogens, antibodies, blood components, environmental pollutants, such as micro-organisms, explosives, and poisons. The devices of the invention are suitable for testing specimens selected, for example, from the group consisting of stool, blood, urine, and saliva, microbe culture media, and swab specimens of surfaces of an animal, such as the cervix, urethra, nostril, and throat, as well as environmental specimens, such as food products, soil and dust samples. By animal is meant, for example, any live or dead animal including, for example, a mammal, for example, a human. Substances to be tested in these specimens include but are not limited to fecal occult blood components, hapto-hemoglobin complex, antibodies, bacteria, viruses, enzymes, proteins, drugs, substances of abuse, allergens, pesticides, and pollutants.

The reagent member can be in liquid, or dry form. In one embodiment of the invention, the reagent member of the test device is a liquid solution comprising reagents capable of reacting with analytes of the sample solution to be tested and produce an assay signal indicative of the presence or quantity of at least one analytes of the sample solution. In another embodiment of the invention, the assay reagent is a dry reagent comprising reagents capable of reacting with analytes of the sample solution to be tested and produce an assay signal indicative of the presence or quantity of at least one analytes of the sample solution. Dry reagents, air-dried or lyophilized, have longer shelf life than liquid reagents. A preferred dry form of assay reagent is, for example, but not limited to, a dry reagent pad, a porous matrix containing the dry assay reagent. Such dry reagents are used for a variety of testing products, such as urine glucose, pH, creatinine, and alcohol test. Another example of a preferred dry reagent member is a lateral flow test strip. Where the reagent member is a dry reagent, for example, a test strip, it is understood by those in the art that the test assembly may comprise more than 1 reagent member, for example, each reagent member comprising reagents for a different analyte detection assay. For example, a device for fecal occult blood test may comprise a reagent member for detecting hemoglobin and another reagent member for detecting hapto-hemoglobin complex.

The present invention also provides kits for detecting test substances in solid, semi-solid, or liquid specimens. For example, provided are kits that comprise a device of the present invention. The kits may further comprise instructions for testing for the presence of a substance in a specimen, and may further comprise instructions for obtaining specimen samples. The kits may further comprise reference samples that may be used to compare test results with the specimen samples.

Example 1

Test Chamber Device for Fecal Occult Blood Test

A fecal occult blood test is an immunoassay based test method for detection of blood in stool specimens. The presence of hemoglobin in feces can be indicative of gastrointestinal tract conditions associated with bleeding such as, for example, colorectal carcinoma, colon polyps, Crohn's disease, and ulcerative colitis. The present example provides a 2-in-1 sample preparation and test device, that does not require liquid pipetting or transfer of the sample or sample solution. A fecal sample is collected and prepared for testing using the fecal collection probe, or sample stick, attached to the cap of the test assembly of the invention. The collection probe is inserted into a fecal specimen at several different sites. Excess sample is removed from the stick by gentle wiping with an absorbent tissue. The probe is reinserted into the tube and the cap is tightened securely. The tube is shaken vigorously to obtain a liquid suspension of the sample. Holding the tube upright, the bottom part of the chamber assembly is loosened about 1 revolution (360°). This allows the sample solution inside of the sample receiving chamber to flow into the test chamber. The device is kept in an upright position for 5 minutes, after which time the results may be read. Waiting for more than 10 minutes may cause the reading to be inaccurate. A negative test is indicated when one rose-pink color band appears in the control zone, meaning that the fecal sample does not contain a detectable level of human hemoglobin. A positive test is indicated when two rose-pink color bands appear, one in the test (T) zone and one in the control (c) zone. A positive result indicates that the specimen contains human hemoglobin. An invalid test is indicated where after five minutes, no bands appear, or a test band appears without a control band appearing.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Singular forms "a", "an", and "the" include plural reference unless the context clearly dictates otherwise. Thus, for example, reference to "a subset" includes a plurality of such subsets, reference to "a nucleic acid" includes one or more nucleic acids and equivalents thereof known to those skilled in the art, and so forth. The term "or" is not meant to be exclusive to one or the terms it designates. For example, as it is used in a phrase of the structure "A or B" may denote A alone, B alone, or both A and B.

Unless defined otherwise, all technical and scientific terms used herein have the same meanings as commonly understood by one of ordinary skill in the art to which this invention belongs. Although any methods and systems similar or equivalent to those described herein can be used in the practice or testing of the present invention, the methods, devices, and materials are now described. All publications mentioned herein are incorporated herein by reference for the purpose of describing and disclosing the processes, systems, and methodologies which are reported in the publications which might be used in connection with the invention. Nothing herein is to be construed as an admission that the invention is not entitled to antedate such disclosure by virtue of prior invention.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, and yet these modifications and improvements are within the scope and spirit of the invention. The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. Thus, the terms and expressions which have been employed are used as terms of description and not of limitation, equivalents of the features shown and described, or portions thereof, are not excluded, and it is recognized that various modifications are possible within the scope of the invention. Embodiments of the invention are set forth in the following claims.

What is claimed is:

1. A device for testing a specimen, comprising
   a. a test assembly, comprising a sample receiving chamber and a test chamber, wherein
   said test chamber comprises an upper end, a lower end, an exterior wall, and a septum wall, said septum wall having a top section that connects to the exterior wall and a bottom section that is separate from the exterior wall,
   said sample receiving chamber is on the interior of said septum wall,
   said sample receiving chamber comprises a bottom hole, which places the sample receiving chamber in fluid communication with the test chamber, and
   said lower end of said test chamber comprises an opening;
   b. at least one reagent member within the test chamber; and
   c. a base capable of being coupled to the opening at the lower end of the test chamber, said base comprising: a handle, an insert section having a thread which engages said opening, and a plug which is effective to seal said hole;
   wherein, when said base is inserted into the lower end of said test chamber, said sample receiving chamber is sealed from said test chamber, and when said base is loosened, said sample receiving chamber is open to said test chamber.

2. The device of claim 1, wherein said base further comprises an o-ring encircling said plug.

3. The device of claim 1, wherein said test assembly further comprises a cap to cover the upper end of said test assembly.

4. The device of claim 3, wherein said cap further comprises a sampler pin.

5. The device of claim 1, wherein said sample receiving chamber further comprises a buffer.

6. The device of claim 1, wherein said reagent member comprises a wick section and a test area comprising an assay reagent.

7. The device of claim 1, wherein said base further comprises an o-ring encircling said insert section.

8. The device of claim 1, comprising at least 2 reagent members.

9. The device of claim 1, comprising from 3-5 reagent members.

10. The device of claim 1, wherein said specimen is solid, semi-solid, or liquid.

11. A device for testing a specimen, comprising
    a. a test assembly comprising an interior wall and an exterior wall that join together at a neck area, forming a test chamber between said interior and exterior walls and a sample receiving chamber within said interior wall,
    and a first breakable seal which seals a lower end opening of the interior wall, such that said sample receiving chamber is sealed from said test chamber;
    b. a reagent member contained within the test chamber;
    c. a bottom part, comprising a hole sealed with a second breakable seal, which part is sized to fit a lower end opening of the exterior wall of said test assembly; and
    d. a pincap comprising a rod;
    wherein, when said bottom part is fitted into said lower end opening of the exterior wall, and said pincap is inserted into said hole of said bottom part, said rod breaks said breakable seals, causing said sample receiving chamber to be open to said test chamber.

12. A kit comprising a device of claim 1 or claim 11 comprising instructions and further comprising a sample buffer.

* * * * *